(12) United States Patent
Gergits (10) Patent No.: US 10,300,220 B2
(45) Date of Patent: May 28, 2019

(54) SURGERY NEEDLE SUPPORT MEMBER (71) Applicant: Franklyn R. Gergits, Bloomsburg, PA (US)

(72) Inventor: Franklyn R. Gergits, Bloomsburg, PA (US)

( * ) Notice: Subject to any disclaimer, the term of this patent is extended or adjusted under 35 U.S.C. 154(b) by 80 days.

(21) Appl. No.: 15/255,728

(22) Filed: Sep. 2, 2016

(65) Prior Publication Data

US 2017/0065774 A1    Mar. 9, 2017

Related U.S. Application Data

(60) Provisional application No. 62/213,914, filed on Sep. 3, 2015.

(51) Int. Cl.
*A61M 5/42* (2006.01)
*A61M 5/46* (2006.01)
*A61M 19/00* (2006.01)

(52) U.S. Cl.
CPC ............. *A61M 5/425* (2013.01); *A61M 5/42* (2013.01); *A61M 5/46* (2013.01); *A61M 19/00* (2013.01); *A61M 2202/048* (2013.01)

(58) Field of Classification Search
CPC .. A61M 19/00; A61M 2202/048; A61M 5/42; A61M 5/425; A61M 5/46
See application file for complete search history.

(56) References Cited

U.S. PATENT DOCUMENTS

| 5,115,816 A | * | 5/1992 | Lee | A61M 5/1782 |
| | | | | 600/562 |
| 5,735,817 A | | 4/1998 | Shantha | |
| 6,491,940 B1 | | 12/2002 | Levin | |
| 7,636,597 B2 | | 12/2009 | Gross et al. | |
| 8,224,438 B2 | | 7/2012 | Levin | |
| 8,229,571 B2 | | 7/2012 | Lorian et al. | |
| 8,954,149 B2 | | 2/2015 | Shalev | |
| 2005/0281751 A1 | | 12/2005 | Levin | |
| 2010/0049230 A1 | | 2/2010 | Benary et al. | |
| 2010/0114184 A1 | | 5/2010 | Degtyar et al. | |
| 2012/0277761 A1 | | 11/2012 | Boling et al. | |
| 2013/0158450 A1 | | 6/2013 | Juto et al. | |

OTHER PUBLICATIONS

Yang, Ian Y., MD et al., A Novel Approach to Transnasal Spenopalatine Ganglion Injection, Pain Physician, vol. 9, pp. 131-134, 2006.

* cited by examiner

*Primary Examiner* — Imani N Hayman
(74) *Attorney, Agent, or Firm* — Panitch Schwarze Belisario & Nadel LLP (57) ABSTRACT

A syringe assembly configured to urge soft tissue out of a surgical path includes a syringe, an elongate support member and a securing member. The syringe includes a barrel, a needle with a needle tip and a plunger movably mounted in the syringe barrel. The syringe defines a longitudinal axis. The elongated support member has a proximal end, a distal end and an arcuate-shaped cross-section. The securing member is fixed near the proximal end of the elongate support member. The securing member is configured to attach the elongate support member to the syringe. A support length is defined between the securing member and the distal end and a tip length is defined between the securing member and the needle tip when the support member is mounted to the syringe. The tip length is greater than the support length when the syringe assembly is in an injection configuration.

13 Claims, 5 Drawing Sheets

SURGERY NEEDLE SUPPORT MEMBER

CROSS-REFERENCE TO RELATED APPLICATIONS

The present application claims the benefit of U.S. Provisional Patent Application No. 62/213,914, filed on Sep. 3, 2015 and titled "Surgical Needle Support Member," the entire contents of which are incorporated herein by reference in its entirety.

BACKGROUND OF THE INVENTION

The present invention is directed to a support sheath for stabilizing, protecting and guiding a surgical needle during a surgical procedure. The support sheath is preferably adapted for stabilizing, protecting and guiding the syringe and needle for injecting anesthesia during a nasal procedure, such as a Sphenopalatine ganglion block.

A variety of invasive facial surgical procedures require entry through the nasal cavity. For example, surgical procedures conducted on the Eustachian tube typically involve entry through the nasal cavity, i.e., intranasal approach. Likewise, a Sphenopalatine ganglion block procedure is a nerve block that is also typically administered through the nasal cavity with relatively small needles and a guidance catheter to inject medication into the area of the Sphenopalatine ganglion. Procedures conducted through the nasal cavity often require the use of relatively small, thin needles. For example, a twenty-seven (27) gauge spinal needle, typically having a diameter of approximately forty-one hundredths of a millimeter (0.41 mm) is often utilized to deliver medication under the mucosal membranes into a targeted area. Such needles are generally malleable and deflectable. One challenge encountered by medical personnel during such surgical procedures is that the nasal cavity (pathway) and beyond includes soft tissue, e.g., mucous membranes and connective tissue that often requires some degree of deflection or manipulation in order to advance the needle to the proper location. The needle is, however, often more easily deflectable than the soft tissue and the needle is deflected by the soft tissue off of the desired path or away from the target area, rather than the soft tissue being deflected out of the way by the needle.

It would, therefore, be advantageous to provide a support sheath having the structural rigidity to deflect or manipulate tissue in the nasal cavity, in order to stabilize and direct the needle into the target area or proper area where medication is injected. It is particularly advantageous to design, manufacture and deploy a surgical needle support member that is removably connectable to the syringe to urge soft tissue out of the surgical path such that a tip or point of the needle may be positioned at the target area where medication injection is desired.

BRIEF SUMMARY OF THE INVENTION

Briefly stated, the preferred invention is directed to a syringe assembly configured to urge soft tissue out of a surgical path includes a syringe, an elongate support member and a securing member. The syringe includes a barrel, a needle with a needle tip and a plunger movably mounted in the syringe barrel. The syringe defines a longitudinal axis. The elongated support member has a proximal end, a distal end and an arcuate-shaped cross-section. The securing member is fixed near the proximal end of the elongate support member. The securing member is configured to attach the elongate support member to the syringe. A support length is defined between the securing member and the distal end and a tip length is defined between the securing member and the needle tip when the support member is mounted to the syringe. The tip length is greater than the support length when the syringe assembly is in an injection configuration.

In another aspect, the preferred invention is directed to a syringe assembly configured to urge soft tissue out of a surgical path. The syringe assembly includes a syringe, an elongate support member and a securing member. The syringe has a syringe barrel, a needle with a needle tip and a plunger movably mounted in the syringe barrel. The syringe defines a longitudinal axis. The elongate support member has an inner surface, a proximal end and a distal end. The elongate support member includes an arcuate-shaped cross-section. A support stop extends away from the inner surface toward the longitudinal axis in a mounted configuration. The securing member is fixed near the proximal end of the elongate support member. The securing member is configured to attach the elongate support member to the syringe. The securing member includes a first clip and a second clip spaced from the first clip. A support length is defined between the second clip and the distal end. A tip length is defined between the second clip and the needle tip in the mounted configuration. The tip length is greater than the support length when the syringe assembly is in an injection configuration and the support stop is contacting the barrel.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Certain terminology is used in the following description for convenience only and is not limiting. Unless specifically set forth herein, the terms "a", "an" and "the" are not limited to one element but instead should be read as meaning "at least one". The words "right," "left," "lower," and "upper" designate directions in the drawings to which reference is made. The words "inwardly" or "distally" and "outwardly" or "proximally" refer to directions toward and away from, respectively, the patient's body, or the geometric center of the preferred surgical needle support device and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally the same or similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-3C a syringe assembly, generally designated 10, in accordance with a first preferred embodiment of the present invention. The syringe assembly 10 is preferably configured to urge soft tissue out of a surgical path, protect a needle 58 from being deflected by soft tissue during insertion and permit injection of a medication, such as anesthesia, at a surgical site with the soft tissue urged out of the surgical path, thereby permitting visualization of the surgical site by the medical professional. The syringe assembly 10 includes a support sheath 11 that is removably mountable onto and selectively movable relative to a syringe 50. The syringe 50 is preferably comprised of a substantially cylindrical syringe barrel 52 having a laterally extending syringe barrel flange 54 proximate an open proximal end of the syringe barrel 52 and a syringe plunger 56 for advancement into the syringe barrel 52 through the open proximal end. A syringe needle 58 may be removably mountable to a distal end of the syringe 50, such as by a Luer lock, to fluidly communicate with the syringe barrel 52. The needle 58 has a tip 58a. The syringe 50 defines a longitudinal axis 48 that is preferably coaxial with the needle 58 and extends through the tip 58a. The support sheath 11 is not necessarily removably mountable to the syringe 50 and may be fixed or secured thereto or integrally formed with the syringe 50.

The first preferred support sheath 11 includes an axially extending support member 12 and at least one flexible, generally arcuate clip 14 extending from a proximal end 12a of the support member 12. In the first preferred embodiment, the arcuate clip 14 is comprised of a first clip 14a positioned near a proximal end 12a of the support member 12 and a second clip 14b spaced from the first clip 14a toward a distal end 12b of the support member 12. The support member 12 preferably extends generally parallel to the longitudinal axis 48 and is radially spaced from the syringe needle 58 substantially along the length of the needle 58 in an assembled or mounted configuration. The support sheath 11 is substantially rotatable around the diameter of the barrel 52 in the first preferred embodiment as the clips 14 are configured to permit diametric movement and selective positioning of the support member 12 relative to the syringe 50. The distal end 12b of the support member 12 may define a rounded tip as well as a bent or curled tip to assist in deflection of soft tissue and other anatomy of the patient, generally without puncturing or otherwise significantly damaging the soft tissue that the support member 12 contacts. The support member 12 is preferably constructed of a polymeric material, such as, for example, without limitation, a biocompatible polymeric material, such as polyethylene, polypropylene, polytetrafluoroethylene, polymethymethacrylate, polyetheretherketone ("PEEK") and other similar materials. The preferred polymeric material is preferably sterilizable, and, therefore, reusable, but is not so limited. The support member 12 and support sheath 11 may alternatively be constructed for single-use functions as a non-sterilizable material. The support member 12 and support sheath 11 may further be constructed of metallic materials, such as stainless steel, aluminum, titanium and materials of similar import that are able to take on the general size and shape of the support member 12 and support sheath 11, withstand the normal operating conditions of these components and perform the preferred functions of the support sheath 11. The support sheath 11 may also be reusable after sterilization, such as following sterilization in an autoclave or other sterilization mechanism or technique.

Figure 1:
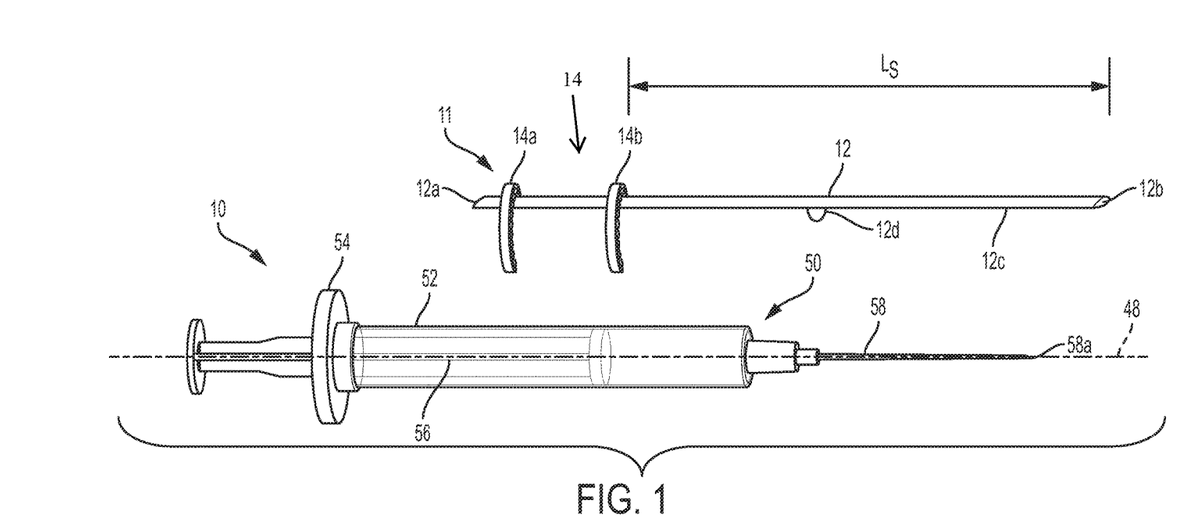
FIG. 1 is a partially exploded, side perspective view of a syringe assembly including a support sheath and a syringe in accordance with a first preferred embodiment of the present invention.
Figure 2:
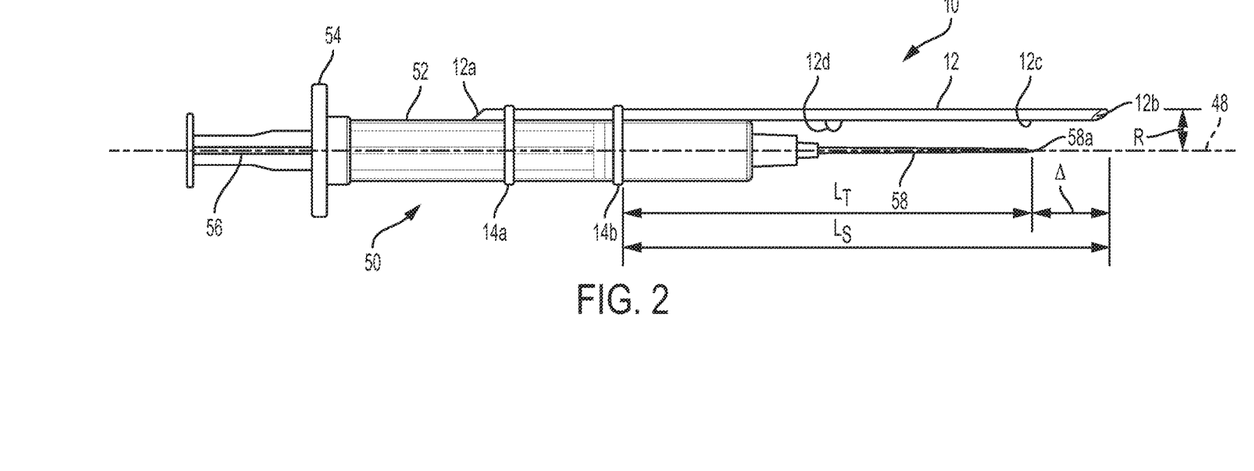
FIG. 2 is a side elevational view of the syringe assembly of FIG. 1, wherein the support sheath is mounted to the syringe.
Figures 3A, 3B, 3C:
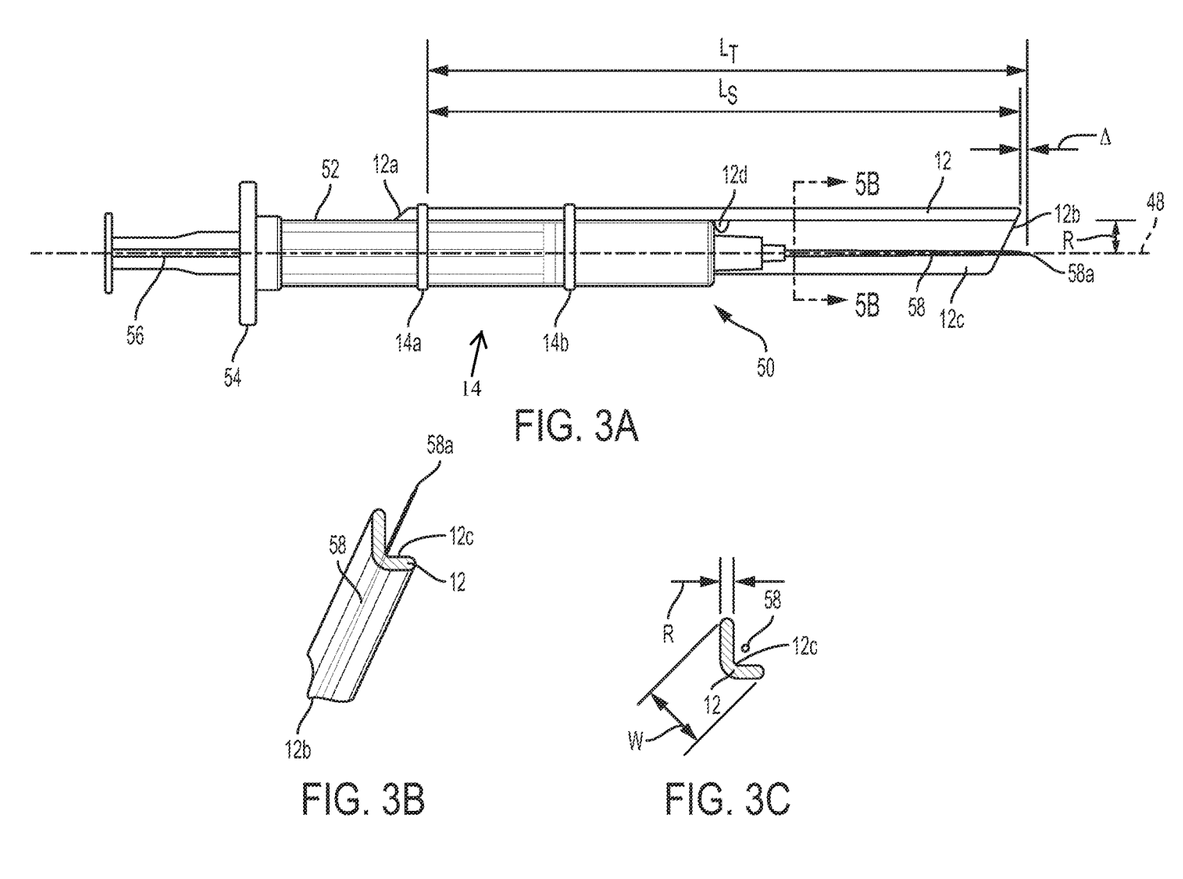
FIG. 3A is a side perspective view of the syringe assembly of FIG. 1, shown in an injection configuration.
FIG. 3B is a rear perspective, cross-sectional view of the support sheath of FIG. 1, taken along line 3B-3B of FIG. 3A.
FIG. 3C is a cross-sectional view of the support sheath of FIG. 1, taken along line 3B-3B of FIG. 3A.

Referring to FIG. 2, the clip 14 comprises the first and second clips 14a, 14b in the first preferred embodiment. Each of the preferred first and second clips 14a, 14b elastically expands and retracts around the syringe barrel 52 to mount the support sheath 11 on the syringe 50 in the assembled configuration. The retraction or clamping force of the clips 14 secures the support sheath 10 to the syringe barrel 52, in combination with friction between the clips 14 and the syringe barrel 52. The clips 14 preferably substantially prevent movement of the support sheath 10 relative to the syringe 50 upon contact with soft tissue during use and, generally, as the syringe 50 with the support sheath 10 mounted thereto are being mounted by the medical professional. The support sheath 11 may also be repositioned on any side of the syringe 50, as desired by the medial professional. That is, the substantially cylindrical shape of the barrel 52 permits mounting of the support sheath 10 at nearly any location around the periphery of the barrel 52. In addition, the generally smooth cylindrical outer surface of the barrel 52 may permit sliding of the support sheath 11 along the barrel 52, substantially parallel to the longitudinal axis 48 for positioning purposes. In the assembled configured, as shown in FIG. 2, the support member 12 extends generally parallel to the syringe needle 58 and the longitudinal axis 48 with a tip 58a of the needle 58 positioned near the distal end 12b of the support member 12. Referring specifically to FIGS. 3B and 3C, the support member 12 preferably has an arcuate cross-section that partially surrounds the needle 58 and arcs generally around the longitudinal axis 51 in the assembled configuration. In the first preferred embodiment, the support member 12 has a substantially frusta-ring-shape with the needle 58 positioned proximate an inner surface 12c of the ring-shape. The support member 12 is not limited to having a frusta-ring-shaped cross-section and may have nearly any size and shape that is able to withstand the normal operating conditions of the support member 12 and perform the preferred functions of the support member 12. For example, the support member 12 may extend approximately one hundred eighty degrees (180°) or less around the needle 58 and longitudinal axis 51 or may have a substantially rod-shape extending along and spaced from the longitudinal axis 58. The support member 12 preferably does not extend completely around the longitudinal axis 51 along the needle 58, particularly proximate the tip 58a to permit visualization of the tip 58a during the procedure.

The support member 12 may also be configured such that its material may be manipulated into alternative curves and shapes to facilitate creation of a surgical pathway to a target area within the patient. Pathways around structures of a patient's nasal cavity are not necessarily straight when approaching a target area and it is desirable for the support sheath 10 to facilitate curved or non-linear pathways. The manipulation of the support member 12 into curved or non-linear shapes facilitates these non-linear pathways and may be designed by the surgeon prior to surgery by pre-operative investigation, planning and manipulation or selection of a curved or bent support member 12 that facilitates the non-straight surgical pathway desired by the surgeon. The syringe needle 58 is also preferably configured for pre-operative shaping for non-linear pathways. In these described non-linear pathway configurations, the needle 58 and support member 12 do not necessarily extend substantially parallel to each other or to the longitudinal axis 51.

Referring to FIGS. 1-3C, the first preferred support sheath 11 has a support length $L_S$ that is defined between the securing member 14 and the distal end 12b. The support length $L_S$ of the first preferred embodiment is specifically defined between the second clip 14b and the distal end 12b. In the first preferred embodiment, the support length $L_S$ is within a range of ten to fifty millimeters (10-50 mm), but is not so limited and may have smaller or larger dimensions depending on the associated syringe 50, the anatomy of the patient, the procedure being performed with the syringe assembly or related design or user preferences. A tip length $L_T$ is also defined by the first preferred syringe assembly 10 between the securing member 14 and the needle tip 58a when the support member 12 is mounted to the syringe 50. In an injection configuration (FIG. 3A), the tip length $L_T$ is greater than the support length $L_S$ such that the tip 58a is exposed beyond the distal end 12b. In this injection configuration, the tip 58a is exposed from the distal end 12b so that the tip 58a may be inserted into the surgical site for injection of the mediation in the barrel 52. The exposure of the tip 58a is represented by a spacing $\Delta$, which is the difference between the tip length $L_T$ and the support length $L_S$. The flange 54 is positioned near and spaced from the first clip 14a in the injection configuration.

The spacing $\Delta$ may be predetermined by particular arrangements of the clip 14 or other mechanical arrangements that predetermine the tip length $L_T$ in the mounted configuration. The first preferred embodiment of the support sheath 11, for example, includes a support stop 12d extending radially inwardly from the inner surface 12c. The support stop 12d is preferably positioned between the securing member 14 and the distal end 12b in the first preferred embodiment. In the injection configuration, the support stop 12d is in facing engagement with a front of the barrel 52 and is positioned such that the tip length $L_T$ is greater than the support length $L_S$ to define the spacing $\Delta$. The support sheath 11 is not limited to being mounted to the syringe 50 with the support stop 12d in facing engagement with the barrel 52 and may be mounted with the support stop 12d spaced from the front end of the barrel 52 such that the support length $L_S$ is greater than the tip length $L_T$ in an introduction or insertion configuration. In the introduction or insertion configuration, the distal end 12b extends beyond the tip 58a along the longitudinal axis 48 such that the support member 12 deflects soft tissue out of the path of the needle 58 during insertion toward the surgical site. The support sheath 11 may subsequently be moved from the insertion configuration to the injection configuration by sliding the clips 14 toward the flange 51. In addition, the syringe assembly 10 is not limited to being positioned in the insertion configuration with the distal end 12b positioned longitudinally forward relative to the tip 58a and may be inserted along the surgical path in the injection configuration while also urging soft tissue out of the surgical path. The partial arcuate configuration or not enclosed configuration of the support member 12 also facilitates visualization of the surgical path and the tip 58a during the insertion process.

The support member 12 is shown in the preferred embodiment as extending substantially parallel to the longitudinal axis 48, but is not so limited. The support member 12 may taper toward the longitudinal axis 48 from its connection to the syringe 50 such that the distal end 12b is closer to the needle 58 than the support member 12 proximate the proximal end 12a or near the hub of the syringe 50. The support member 12 may taper relatively consistently toward the longitudinal axis 48 or may be configured such that a significant portion of the support member 12 extends generally parallel to the longitudinal axis 48 until tapering toward the longitudinal axis 48 proximate the distal end 12b. For example, the last one centimeter (1 cm) of the support member 12 near the distal end 12b may bend at an angle of approximately fifteen to forty-five degrees (15-45°) toward the longitudinal axis 48 and the tip 58a. Most preferably, the support member 12 bends at preferred angles of fifteen, thirty or forty-five degrees (15°, 30° or 45°) to extend to a position near the tip 58a. This angulation or tapering of the distal end 12b toward the tip 58a facilitates urging of soft tissue away from the surgical site and injection of the medication into the surgical site by the surgeon or medical technician. In this preferred tapering configuration, the radial distance R changes as the support member 12 extends toward the tip 58a.

Referring to FIGS. 3A-3C, in the first preferred embodiment, the support member 12 has a width W measured substantially perpendicular to the longitudinal axis 48. The width W provides a lateral shield to the needle 58 for blocking or shielding the needle 58 from soft tissue during insertion of the syringe assembly 10 toward the surgical site. The width W is preferably limited to arcuately extending only around a diametric portion of the needle 58 relative to the longitudinal axis 48. Specifically, the width W is preferably limited such that the support member 12 does not extend diametrically around greater than one hundred eighty degrees (180°) relative to the longitudinal axis 48. The limitation of the width W permits improved visualization of the needle 58 and, particularly the tip 58a during use such that the medical professional is able to visually track the movement of the needle 58 and the tip 58a during insertion to the surgical site and when the tip 58a reaches the surgical site to facilitate injection of the medication at the preferred location in the patient's anatomy. The first preferred support member 12 may, for example, have a relatively narrow width 12 such that the support member 12 has a substantially shaft-type configuration or may have a larger width 12 such that the support member 12 has an arcuate, paddle-like configuration. When the support member 12 has a relatively larger width W, the support member 12 has a substantially frusta-ring cross-sectional shape. In the first preferred embodiment, the needle 58 is spaced at a radial distance R from the inner surface 12c such that relatively modest deflections of the support member 12 by soft tissue during insertion generally does not impact the surgical pathway of the needle 58. In the first preferred embodiment, the radial distance R is approximately three to nineteen millimeters (3-19 mm), but is not so limited and may have smaller or greater sizes, depending on the side of the syringe 50, the anatomy of the patient or related considerations of the designer or user of the syringe assembly 10.

Figure 4:
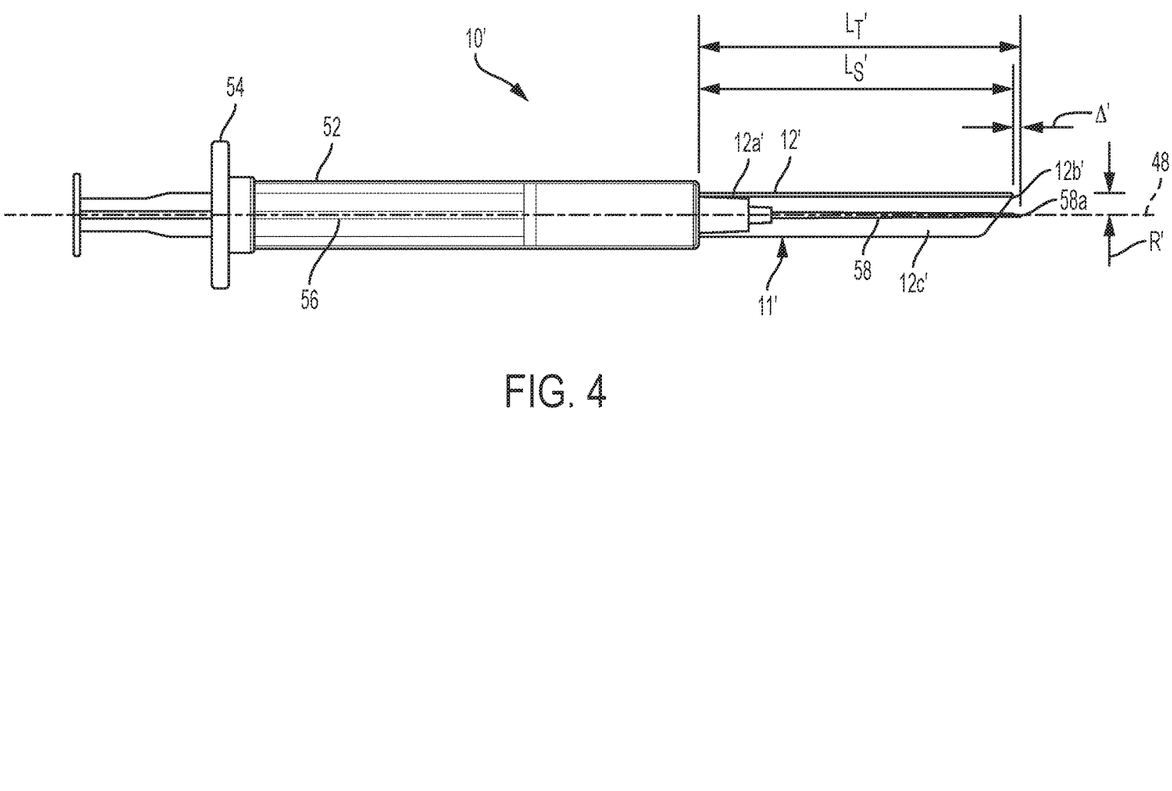
FIG. 4 is a side elevational view of a support sheath, in accordance with a second preferred embodiment of the present invention mounted on the syringe.

Referring to FIG. 4, a support sheath 11' in accordance with a second preferred embodiment includes a support member 12' that fits substantially around and is radially spaced at the radial distance R from the needle 58. The support sheath 11' removably attaches to the distal end of the syringe barrel 52. Similar reference numbers are utilized to identify similar features of the second preferred embodiment of the support sheath 11' with features of the first preferred embodiment of the support sheath 11, with a prime symbol (') used to distinguish the features of the second preferred embodiment. The proximal end of the support sheath 11' is configured to removably and fittingly attach to a syringe hub 53. The support sheath 11' may be removably and fittingly attached to the syringe hub 53 by a Luer lock mechanism or other needle attachment mechanism (not shown), such as clamping, fastening, adhesively bonding or snap fitting, at the distal end or syringe hub 53 of the syringe barrel 52. The support sheath 11' is preferably fixed to the syringe 50 in the mounted configuration and may be removed from the syringe 50 by releasing the locking mechanism. The needle 58 preferably extends substantially parallel to and coaxially with the longitudinal axis 48. The needle 58 also preferably extends generally parallel to and proximate the inner surface 12c' of the support member 12' such that the inner surface 12c' is spaced from the longitudinal axis 48 at the radial distance R'. Similar to the first preferred embodiment of FIGS. 1-3C, the support member 10' of the second preferred embodiment may be constructed of a biocompatible polymeric material, such as a surgical grade plastic, a metallic material or, alternatively, of a non-sterilizable polymeric or other material. The support member 12' is preferably an integrally formed component, but is not so limited and may be comprised of an assembly of a first portion and a second portion (not shown) that a movable relative to each other substantially parallel to the longitudinal axis 48 such that the distal end 12b' may be moved relative to the syringe tip 58a in the mounted configuration to change the spacing Δ' of the distal end 12b' relative to the syringe tip 58a.

In one exemplary operation, the support sheath 11, 11' of the first or second preferred embodiments may be utilized during a sphenopalatine ganglion block procedure. During the procedure, the support sheath 11, 11' is mounted on the syringe 50. The clips 14 of the support sheath 11 of the first preferred embodiment are snapped onto the syringe barrel 52 or the locking mechanism at the proximal end of the second preferred support sheath 11' is connected to the syringe hub 53, as described above. The syringe 50, for example, may include a thin gauge spinal needle 58, such as a twenty-seven (27) gauge needle 58 or a similar needle 58. The syringe 50 and attached support sheath 10, 10' is thereafter advanced through the nasal cavity of a patient, through the sphenopalatine foramen, and to the pterygopalatine fossa where the sphenopalatine ganglion is located. During such advancement, the support member 12, 12' deflects soft tissue encountered, e.g., mucous membrane and connective tissue, sufficiently out of the path of the spinal needle 58, in order to reach the sphenopalatine ganglion. Once the desired location is reached, the ganglion is injected with anesthetic to achieve a sphenopalatine ganglion block. The tip 58a of the needle 58 preferably extends beyond the distal end 12b, 12b' of the support member 12, 12' in the injection configuration such that the needle 58 is insertable into the ganglion before contacting the distal end 12b, 12b'.

Figure 5A:
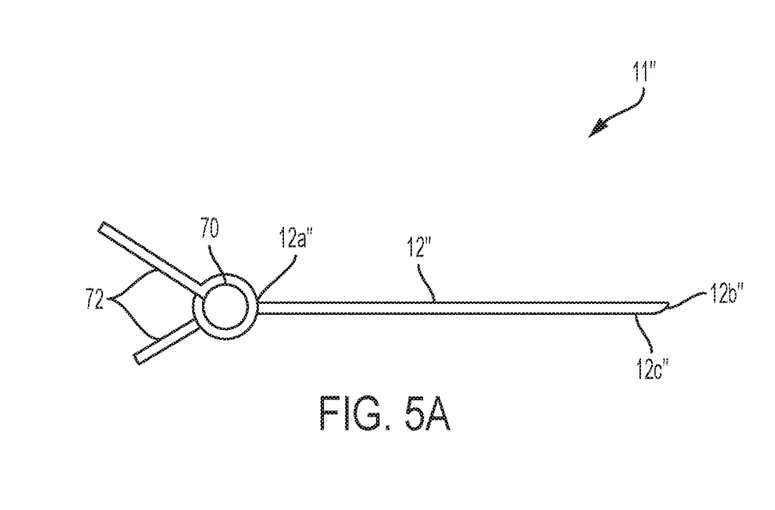
FIG. 5A is a side elevational view of a support sheath, in accordance with a third preferred embodiment of the present invention.
Figure 5B:
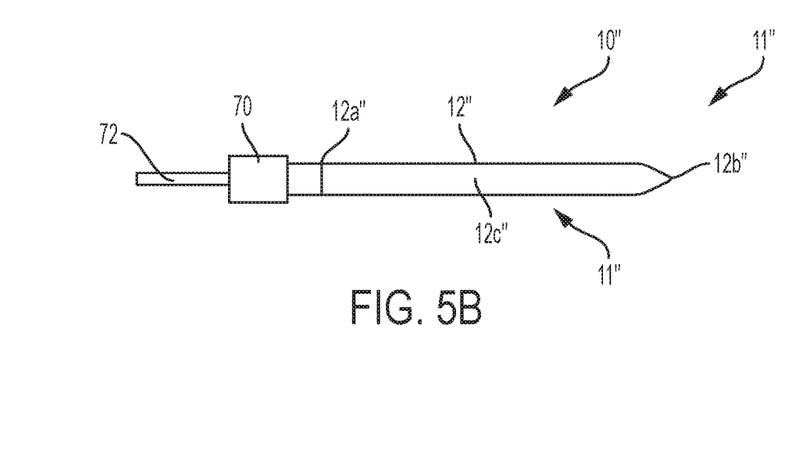
FIG. 5B is an top plan view of the support sheath of FIG. 5A.

Referring to FIGS. 5A and 5B, in a third preferred embodiment, a support sheath 10" in accordance with the third preferred embodiment includes a support member 12" that fits over the needle 58 and removably attaches to the syringe barrel 52. Similar reference numbers are utilized to identify similar features of the third preferred embodiment of the support sheath 11" with features of the first and second preferred embodiments of the support sheath 11, 11', with a double-prime symbol (") used to identify the features of the third preferred embodiment. The support sheath 11" of the third preferred embodiment is configured similar to a clothes pin with relatively long legs that comprise the support member 12". The support sheath 11" is preferably clipped to the syringe 50 with the distal end 12b" of the support member 12" positioned proximate the tip 58a of the needle 58. The support sheath 11" preferably includes a hinge 70 and pivot arms 72 that facilitate clipping or attaching the support sheath 11" to the syringe 58 and removing the support member 12" from the syringe 50.

Figure 6:
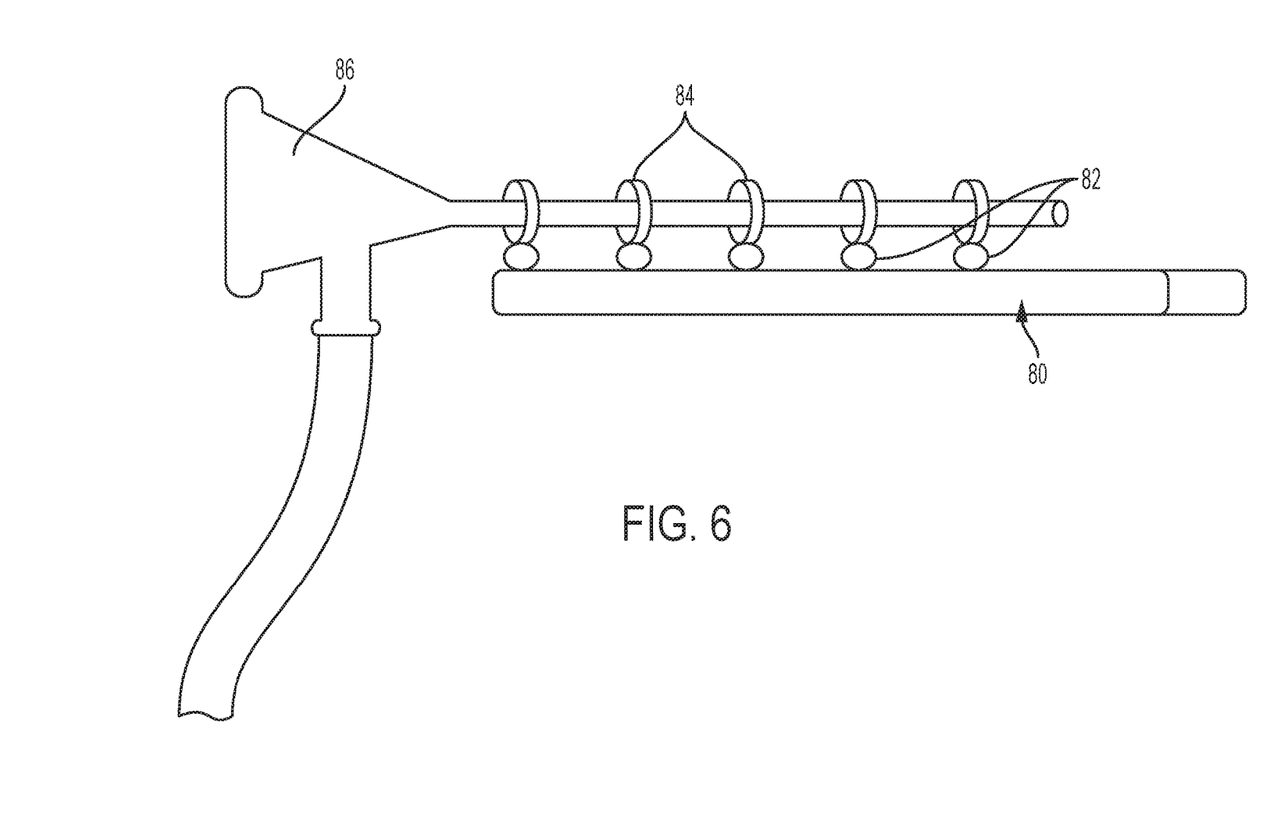
FIG. 6 is a side elevational view of a scope, sheaths and an elevator in accordance with a fourth preferred embodiment of the present invention.

Referring to FIG. 6, the preferred support sheaths 10, 10', 10" may be utilized with an elevator 80 that includes hinges 82 and is attached to a scope 86 with sheaths 84. The scope 86 is utilized to provide visualization during the nasal surgery. The scope 86 may also include a suction (not shown) associated with the elevator 80 that is removably attached to the scope 86 and is able to suction blood and mucus from the surgical path during use. The suction may also be utilized with the preferred support sheaths 10, 10', 10" to provide suction during use.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the disclosure.

I claim:

1. A syringe assembly configured to urge soft tissue out of a surgical path, the syringe assembly comprising:
   a syringe having a syringe barrel, a needle with a needle tip and a plunger movably mounted in the syringe barrel, the syringe defining a longitudinal axis;
   an elongated support member having a proximal end and a distal end, the elongate support member having an arcuate-shaped cross-section and a support stop extending radially inwardly from an inner surface of the support member; and
   a securing member fixed near the proximal end of the elongate support member, the securing member configured to attach the elongate support member to the syringe, a support length defined between the securing member and the distal end, a tip length defined between the securing member and the needle tip when the support member is mounted to the syringe, the tip length being greater than the support length when the syringe assembly is in an injection configuration and the support length being greater than the tip length when the syringe assembly is in an insertion configuration.

2. The syringe assembly of claim 1, wherein the support stop is positioned between the securing member and the distal end.

3. The syringe assembly of claim 1, wherein the support stop is in facing engagement with the syringe in the injection configuration.

4. The syringe assembly of claim 1, wherein the support member is rotatable around the longitudinal axis when the securing member mounts the support member to the syringe.

5. The syringe assembly of claim 1, wherein the support member has a frusta-ring cross-sectional shape.

6. The syringe assembly of claim 1, wherein an internal surface of the support member is spaced from the longitudinal axis at a radial distance.

7. The syringe assembly of claim 6, wherein the radial distance is approximately three to nineteen millimeters.

8. The syringe assembly of claim 1, wherein the support length is within a range of ten millimeters to fifty millimeters.

9. The syringe assembly of claim 1, wherein the securing member is comprised of a first securing clip and a second securing clip, the first clip spaced from the second clip.

10. The syringe assembly of claim 9, wherein the support length is defined between the second clip and the distal end.

11. A syringe assembly configured to urge soft tissue out of a surgical path, the syringe assembly comprising:
a syringe having a syringe barrel, a needle with a needle tip and a plunger movably mounted in the syringe barrel, the syringe defining a longitudinal axis;
an elongate support member having an inner surface, a proximal end and a distal end, the elongate support member having an arcuate-shaped cross-section, a support stop extending away from the inner surface toward the longitudinal axis in a mounted configuration; and
a securing member fixed near the proximal end of the elongate support member, the securing member configured to attach the elongate support member to the barrel, the securing member including a first clip and a second clip spaced from the first clip, the support stop positioned between the second clip and the distal end, a support length defined between the second clip and the distal end, a tip length defined between the second clip and the needle tip in the mounted configuration, the tip length being greater than the support length when the syringe assembly is in an injection configuration and the support stop is contacting the barrel.

12. The syringe assembly of claim 11, wherein the support length is within a range of ten millimeters to fifty millimeters.

13. The syringe assembly of claim 11, wherein the syringe includes a flange near a proximal syringe end, the first clip spaced from the flange in the injection configuration.

\* \* \* \* \*